United States Patent [19]

deWijn

[11] 4,093,576

[45] June 6, 1978

[54] MIXTURE FOR ANCHORING BONE IMPLANTS

[75] Inventor: Joost Robert deWijn, Nijmwegen, Netherlands

[73] Assignee: Sulzer Brothers, Ltd., Winterthur, Switzerland

[21] Appl. No.: 673,354

[22] Filed: Apr. 5, 1976

[30] Foreign Application Priority Data

Apr. 18, 1975 Switzerland ............... 4970/75

[51] Int. Cl.$^2$ ............................................. C08L 1/28
[52] U.S. Cl. ................................. 260/17 R; 32/15; 128/92 R; 128/92 C; 128/92 CA; 128/92 G; 260/17.4 ST; 260/29.6 WA; 260/901; 424/80; 424/78; 424/81
[58] Field of Search ............ 260/17 R, 29.6 WA, 901, 260/17.4; 424/80, 78; 128/92 R, 92 C, 92 CA, 92 B, 92 G; 32/15

[56] References Cited

U.S. PATENT DOCUMENTS

| | | | |
|---|---|---|---|
| 3,030,951 | 4/1962 | Mandarino | 128/92 G |
| 3,483,870 | 12/1969 | Coover et al. | 424/81 |
| 3,736,274 | 5/1973 | Schoenholz et al. | 428/80 |
| 3,787,900 | 1/1974 | McGee | 32/15 |
| 3,866,248 | 2/1975 | Kummer | 128/92 C |
| 3,882,080 | 5/1975 | Schmitt et al. | 260/901 |
| 3,882,858 | 5/1975 | Klemm | 128/92 G |
| 3,924,274 | 12/1975 | Heimke | 128/92 C |

OTHER PUBLICATIONS

Chem. Absts., vol. 81: 82347c, "New Improved Bone Cement," Iida et al.

Primary Examiner—Edward M. Woodberry
Attorney, Agent, or Firm—Kenyon & Kenyon, Reilly, Carr & Chapin

[57] ABSTRACT

The doughy bone cement mixture is formed by mixing a powder-form polymer, such as polymethylmethacrylate, with a polymerizing liquid monomer, such as a liquid monomeric methylmethacrylate, to form a water-insoluble composition and admixing this composition with a biologically-compatible high-viscosity aqueous gel to form a dispersion of the composition with the gel. The gel is soluble in water as well as in body fluids so as to dissolve out after implanting of an implant or joint end in a bone. This allows the remaining component of the cement to become porous and, thus, allows for tissue invasion over a course of time to further anchor the implant or joint end. The gel may consist of partially neutralized, carboxymethyl cellulose dissolved in water.

14 Claims, No Drawings

MIXTURE FOR ANCHORING BONE IMPLANTS

This invention relates to a bone cement and particularly to a bone cement for anchoring bone implants and prosthetic joint ends in a bone.

Conventionally, two different procedures are known for anchoring implants and prosthetic joint ends in a bone. In one procedure, prostheses are cemented into the bone by means of bone cements, which are basically mixtures consisting of plastics which contain an ingredient which cures the mixture in the bone. In the second procedure, the prostheses parts to be anchored in the bone have a porous surface whose pores are invaded by bone tissue in the course of time. There are disadvantages in both procedures.

The procedure in which bone cements are cured is associated with a considerable temperature rise which may damage and cause necroses of the layers of bone immediately adjacent the cement. For the tissue invasion method to be satisfactory, the prosthesis must remain fixed and immobile for at least several weeks relative to the surrounding tissue. It is very difficult to achieve immobilization of this order in practice, and the necessary immobilization may be very detrimental to a patient's general condition.

Accordingly, it is an object of the invention to improve the means for anchoring implants in bone and to reduce the disadvantages of the known forms of anchorage.

Briefly, the invention provides a bone cement mixture which is a dispersion of a water-insoluble composition with a biologically compatible high-viscosity gel which is soluble in water or body fluid. The term "high viscosity" as used herein refers to viscosities of 200,000 centipoise or more. High viscosities of this level are necessary to prevent demixing of the water-soluble and water-insoluble dispersion ingredients.

Admixing an aqueous gel to a conventional bone cement considerably reduces the maximum temperature occuring during curing so as to prevent the necrosis mentioned above. Also, after an operation, the aqueous gel component of the mixture dissolves in the body's own fluids. Consequently, a network of open intercommunicating pores arises in the bed of bone cement around the implant. Since the low maximum reaction temperature occurring in the polymerization reaction obviates necrotic damage of the ambient tissue, the pores are invaded quite soon by bone tissue. Such invasion leads to a very strong anchorage of the cement bed in the bone without the need for prolonged immobilization of the implants. Also, the cementing of the implant into the bone gives a strong primary anchorage right from the start.

Advantageously, the gel can consist of at least one of the substances polyvinylalcohol (PVAL), polyhydroxyalkylmethacrylate, polyvinylmethyl ether, polyvinylpyrrolidone, a polyacrylic acid salt, a water-soluble polysaccharide or a water-soluble cellulose ether more particularly partialy neutralized carboxymethylcellulose (CMC); such substance having been dissolved in an aqueous liquid in a quantity of from 3 to 60 percent by weight.

The amount of porosity remaining after dissolution of the gel can be varied by variation of the proportion of gel in the mixture. In this connection, it has been found advantageous if the gel is present in the mixture in a proportion such that a network of continuous gel filaments is present in the dispersion. Advantageously, this can be achieved by mixtures containing from 3 to 50 percent by weight gel.

The mechanical strengths of a cured and deliberately porous bone cement bed according to the invention are less than the mechanical strengths of a conventional solid cement body which is of unavoidable porosity because of inclusions of gas and liquid. Very advantageously, therefore, the water-insoluble composition used in the mixture is a known bone cement which exhibits a very reduced unavoidable self-porosity in curing. It has therefore been found convenient if the water-insoluble composition consists of at least powder-form polymethylmethacrylate (PMMA) and of liquid monomeric methylmethacrylate (MMA), up to five percent (5%) by weight of the liquid ingredient being a tertiary amine and from 10 to 45 percent by weight being at least one monovalent monofunctional methacrylic acid ester selected from the group containing saturated aliphatic alcohol ingredients having from 2 to 6 carbon atoms in the alcohol radical e.g. ethyl-, propyl-, butyl-, isopropyl-, isobutyl-, isopentyl-, isobutyl- and pentyl-methacrylate. Additives containing polymerization catalysts and/or polymerization accelerators, X-ray contrast agents and stabilizers may also be added in powder or liquid form.

It is also possible for the gel to have an admixture of other substances, e.g. substances which improve bone formation, such as calcium phosphate, and/or buffer solutions to maintain the gel at a predetermined pH value and/or antibiotics and other medicaments, e.g. for improved post-operative antisepsis. Because of the continuous gel filaments in the mixture, these other substances can be dissolved and can become operative substantially throughout the entire volume of the cement bed. Thus, much smaller quantities of such substances are required for a comparable effect than in the prior art, where such substances are, for example an ingredient of the powder-form components, and only a surface proportion of the substances can be operative.

The high viscosities of the cement composition and gel may sometimes cause difficulties in preparing and homogenizing the mixture. The following sequence of operations in combining the ingredients is therefore recommended to ensure a satisfactory uniform distribution of the various ingredients in the dispersion:
 (a) mixing the powder-form ingredient of the water-insoluble composition with the powder-form gelling agent;
 (b) adding and admixing the liquid ingredient of the water-insoluble composition, and
 (c) adding and admixing the liquid necessary to produce gelling.

The invention will be described in greater detail hereinafter with reference to two embodiments.

The water-insoluble composition used in the two examples is a known commercially available bone cement consisting of a powder-form ingredient containing 90 parts by weight of polymethylmethacrylate (PMMA) as filler, 10 parts by weight of zirconia as X-ray contrast agent and 2 parts by weight of benzoyl peroxide as polymerization catalyst, and a liquid ingredient containing as curing monomer 85 parts of methylmethacrylate (MMA) and 15 parts of n-butylmethacrylate and, as polymerization accelerator, 2 parts of N-dimethyl-p-toluidine.

The gel used in both the examples is prepared by means of commercially available carboxymethylcellulose (CMC) of a particular specification characterized by the following particulars:

Degree of substitution in carboxylation of alcohol radicals: 1.18;

pH value of 0.5% aqueous solution: 6.8;

Viscosity, measured by capillary viscosimeter, of a 1% aqueous solution at ambient temperature: 390 centipoise.

The CMC gels used have a CMC component of from 5 to 30 parts dissolved in from 95 to 70 parts of water. Their viscosity, which was determined — if measurable at all — by means of an LVT Brookfield viscosimeter with spindle 4 at 3 revolutions per minute is several hundred thousand centipoise at ambient temperature.

To study the properties, such as porosity, compressive strength, formation of interconnected gel filaments in the mixture — the latter can be found e.g. by electrical conductivity measurements —, and the like, 20 parts of the powder-form component of the water-insoluble composition are first mixed with 6 parts of CMC powder by hand until the two powders have been thoroughly mixed together. Thereafter, the liquid ingredient of the cement composition is added and admixed, also manually. Next, 14 parts of the water necessary for gelling are added and mixed in.

During mixing both the curing of the cement and the gelling from CMC and water occur. The mixture described, which forms a bone cement having a 40% gel component, the gel containing 30% CMC, is used for the tests indicated, the gel being washed out with water before tests with or on a porous cement skeleton.

The advantage of the procedure described for preparing the mixture is that there is no need to mix together two high-viscosity doughy and gel-like ingredients. Instead, there is a relatively simple mixing together of two powders, gelling occurring in the mixed powder.

Of course, the CMC proportion in the gel and/or the gel proportion in the mixture can be varied by using different proportions of the ingredients described.

As previously stated, the curing temperatures used in the experiment are greatly reduced. The curing times, which have of course been defined as the time between the mixing together of the liquid and powder-form ingredients of the bone cements until the maximum temperature is reached, are substantially the same as for a cement having the composition described but not mixed with the gel. Of course, the porosity of the mixture varies with the amount of gel. As the proportion of gel increases, the porosity, which in the tests is higher by a substantially constant amount of from 7 to 10% than the percentage of gel in the mixture, increases while mechanical strength decreases. Pore diameter is in a range of from about 50 to 150 μm, a very satisfactory figure for biological purposes. It may in some circumstances be possible to vary pore diameters in the bone cement structure by variation of the grain size and/or the shape of the discrete particle of the powder-form CMC.

In the second example, serving for tests in vivo, 10 parts of powder of the same bone cement are first mixed with 4 parts of its liquid component manually in a conventional manner. The doughy composition is then mixed very intimately, again manually, with 8 parts of a CMC gel, this mixture then being used for experiments in the bones of experimental animals.

The gel used in this case consists of 95 parts of water and 5 parts of CMC of the specification mentioned and has a viscosity of more than 300,000 centipoise.

The in vivo tests show a total absence of necrotic damage of the bone tissue. The tests also confirm that the gel is dissolved by body fluid out of the cement skeleton whose intercommunicating open pores are then invaded within a few weeks by vascularized bone tissue.

What is claimed is:

1. A doughy mixture for anchoring implants and prosthetic joint ends in bones, said mixture comprising a water-insoluble composition of a filler consisting of at least one polymethylmethacrylate (PMMA) polymer in powder form and a polymerizing liquid monomeric methylmethacrylate (MMA) monomer; and a biologically compatible high-viscosity gel of 200,000 centipoise or more in admixture with said water-insoluble composition to form a dispersion of said composition with said gel, said gel being soluble in water and in body fluid and being selected from the group consisting of polyvinylalcohol (PVAL), polyhydroxy alkylmethacrylate, polyvinylmethyl ether, polyvinylpyrrolidone, a polyacrylic acid salt, a water-soluble polysaccharide or a water-soluble cellulose ether more particularly partially neutralized carboxymethylcellulose (CMC); such substance having been dissolved in an aqueous liquid in a quantity of from 3 to 60 percent by weight.

2. A mixture as set forth in claim 1 wherein said gel is present in said mixture in a proportion sufficient to form continuous gel filaments in said dispersion.

3. A mixture as set forth in claim 1 wherein said liquid monomer contains up to five percent (5%) by weight of a tertiary amine, and from 10 to 45 percent by weight of at least one monomeric methacrylate selected from the group consisting of ethyl-, propyl-, butyl-, isopropyl-, isobutyl-, isopentyl-, isobutyl- and pentyl-methacrylate.

4. A mixture as set forth in claim 1 wherein said gel consists of partialy neutralized carboxymethylcellulose.

5. A mixture as set forth in claim 2 wherein said gel constitutes 3 to 50 percent by weight of the mixture.

6. A mixture as set forth in claim 1 wherein said gel has an admixture of substances for promoting bone formation, said substances containing calcium phosphate.

7. A mixture as set forth in claim 6 wherein said gel has an admixture of at least one buffer solution to maintain a predetermined pH value of said gel.

8. A mixture as set forth in claim 1 wherein said gel has an admixture of an antibiotic.

9. A doughy water-insoluble bone cement consisting of a water-insoluble composition of at least one polymethylmethacrylate (PMMA) polymer in powder form and a polymerizing monomeric methmethacrylate (MMA) monomer in liquid form; and a biologically compatible high viscosity gel of 200,000 centipose or more in admixture with said water-insoluble composition to form a dispersion of said composition with said gel, said gel being soluble in body fluid whereby upon dissolution of said gel a porous bone cement bed is formed of said composition, said gel being selected from the group consisting of polyvinylalcohol (PVAL), polyhydroxy alkylmethacrylate, polyvinylmethyl ether, polyvinylpyrrolidone, a polyacrylic acid salt, a water-soluble polysaccharide or a water-soluble cellulose ether more particularly partially neutralized carboxymethycellulose (CMC); such substance having been dissolved in an aqueous liquid in a quantity of from 3 to 60 percent by weight.

10. A process of producing a dough-like bone cement for hardening in situ to form a porous bone-cement bed, said process comprising the steps of
mixing a powder-form water-insoluble polymethylmethacrylate (PMMA) polymer composition with a powder-form gelling agent of 200,000 centipoise of more viscosity, said gelling agent being selected from the group consisting of polyvinylalcohol (PVAL), polyhydroxyalkylmethacrylate, polyvinylmethyl ether, polyvinylpyrrolidone, a polyacrylic acid salt, a water-soluble polysaccharide or a water-soluble cellulose ether more particularly partially neutralized carboxymethycellulose (CMC); such substance having been dissolved in an aqueous liquid in a quantity of from 3 to 60 percent by weight:
adding and admixing a liquid polymerizing monomeric methacrylate, and
adding and admixing an amount of liquid necessary to produce gelling.

11. A process as set forth in claim 10 wherein the gelling agent is a carboxymethyl cellulose.

12. A process of producing a dough-like bone-cement for hardening in situ to form a porous bone cement bed; said process comprising the steps of
mixing together at least one powdered polymethymethacrylate (PMMA) polymer, a polymerizing fluid monomeric methylmethacrylate (MMA) and a biologically compatible highly viscous water-soluble gel of 200,000 centipoise or more being selected from the group consisting of polyvinylalcohol (PVAL), polyhydroxy alkyl methacrylate, polyvinylmethyl ether, polyvinylpyrrolidone, a polyacrylic acid salt, a water-soluble polysaccharide or a water-soluble cellulose ether more particularly partially neutralized carboxymethy-cellulose (CMC); such substance having been dissolved in an aqueous liquid in a quantity of from 3 to 60 percent by weight to form a dispersion while curing said polymer and gelling said gel to form a biologically compatible water-insoluble dough-like mass.

13. In a process of anchoring implants, the steps of
mixing together at least one powdered polymethymethacrylate (PMMA) polymer, a polymerizing fluid monomeric methylmethacrylate (MMA) monomer and a biologically compatible highly viscous water-soluble gel of 200,000 centipoise or more, said gel being selected from the group consisting of polyvinylalcohol (PVAL), polyhydroxy alkyl methacrylate, polyvinylmethyl ether, polyvinylpyrrolidone, a polyacrylic acid salt, a water-soluble polysaccharide or a water-soluble cellulose ether more particularly partially neutralized carboxymethy-cellulose (CMC); such substance having been dissolved in an aqueous liquid in a quantity of from 3 to 6 percent by weight to form a dispersion while curing said polymer and gelling said gel to form a biologically compatible water-insoluble dough-like mass;
placing the dough-like mass in a bone;
hardening the placed dough-like mass in the bone; and
thereafter dissolving the gel from said hardened mass to form a porous bone cement bed capable of being invaded by bone tissue for anchoring of said bed in the bone.

14. A doughy mixture for anchoring implants and prosthetic joint ends in bones, said mixture comprising
a water-insoluble composition of a filler consisting of at least one methylmethacrylate polymer in powder form and a liquid ingredient containing a polymerizing liquid methylmethacrylate monomer and n-butylmethacrylate; and
a biologically compatible high-viscosity gel of 200,000 centipoise or more in admixture with said water-insoluble composition to form a dispersion of said composition with said gel, said gel being soluble in water and in body fluid and being at least one of the substances selected from the group consisting of polyvinylalcohol (PVAL), polyhydroxy alkylmethacrylate, polyvinylmethyl ether, polyvinylpyrrolidone, a polyacrylic acid salt, and a water soluble polysacharide, said substance having been dissolved in an aqueous liquid in a quantity of from 3 to 60 percent by weight.

* * * * *

UNITED STATES PATENT AND TRADEMARK OFFICE
CERTIFICATE OF CORRECTION

PATENT NO. : 4,093,576
DATED : June 6, 1978
INVENTOR(S) : Joost Robert deWijn

It is certified that error appears in the above-identified patent and that said Letters Patent are hereby corrected as shown below:

Column 1, line 59, change "partialy" to --partially--

Column 4, line 39, change "partialy" to --partially--

Column 4, lines 55-56 change "methmetharcrylate" to

--methylmethacrylate--

Column 4, line 58, change "centipose" to --centipoise--

Column 5, lines 29-30 change "polymethymethacrylate" to

--polymethylmethacrylate--
Column 6, lines 2-3 change "polymethymethacrylate" to
--polymethylmethlacrylate--
Column 6, line 15, change "3 to 6" to --three(3) to sixty(60)--
Column 6, line 42, change "polysachoride" to --
--polysaccharide--

Signed and Sealed this

Fifth Day of December 1978

[SEAL]

Attest:

RUTH C. MASON
Attesting Officer

DONALD W. BANNER
Commissioner of Patents and Trademarks